United States Patent [19]
Kelly et al.

[11] Patent Number: 5,648,351
[45] Date of Patent: Jul. 15, 1997

[54] USE OF MACROLIDES FOR THE TREATMENT OF CEREBRAL ISCHEMIA

[75] Inventors: John S. Kelly; Steven P. Butcher; John Sharkey, all of Edinburgh, United Kingdom

[73] Assignee: Fujisawa Pharmaceutical Co., Ltd., Osaka, Japan

[21] Appl. No.: 464,815

[22] PCT Filed: Dec. 24, 1993

[86] PCT No.: PCT/JP93/01886

§ 371 Date: Jun. 29, 1995

§ 102(e) Date: Jun. 29, 1995

[87] PCT Pub. No.: WO94/14443

PCT Pub. Date: Jul. 7, 1994

[30] Foreign Application Priority Data

Dec. 29, 1992 [GB] United Kingdom ............ 9227055

[51] Int. Cl.$^6$ ................................................ A61K 31/33
[52] U.S. Cl. ............................................................ 514/183
[58] Field of Search ................................................ 514/183

[56] References Cited

U.S. PATENT DOCUMENTS 5,266,594  11/1993  Dawson et al. ........................ 514/560

FOREIGN PATENT DOCUMENTS

| 0 184 162 | 6/1986 | European Pat. Off. . |
| 2 248 184 | 4/1992 | United Kingdom . |
| WO89/05304 | 6/1989 | WIPO . |
| WO91/17754 | 11/1991 | WIPO . |

OTHER PUBLICATIONS

Brian Research, vol. 595, No. 1, pp. 145–148, (1992), Y. Shiga, et al., "Cyclosporin a Protects Against Ischemia–Reperfusion Injury in the Brain".

Proc. Natl. Acad. Sci., vol. 90, pp. 9808–9812, Nov. (1993), T. Dawson, et al., "Immunosuppresant FK506 Enhances Phosphorylation of Nitric Oxide Synthase and Protects Against Glutamate Neurotoxicity".

The New York Times Science, May 25, (1993), G. Kolata, "Brain Researcher Makes It Look Easy", pp. B6–B7.

Primary Examiner—Raymond Henley, III
Attorney, Agent, or Firm—Oblon, Spivak, McClelland, Maier & Neustadt, P.C.

[57] ABSTRACT

The present invention relates to a new use of macrolide compounds of the formula (I):

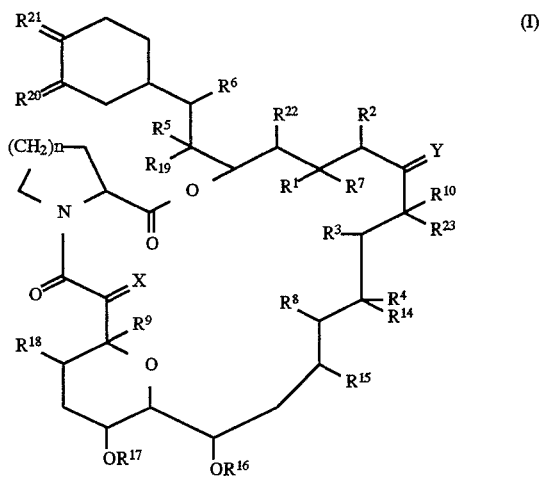

wherein each symbol is as defined in the specification, for preventing or treating cerebral ischemic disease, such as, brain damage caused by ischemia, such as cerebral infarction. So, they are useful when the following diseases or injury occur. That is, head injury, hemorrhage in brain such as subarachnoid hemorrhage or intracerebral hemorrhage, cerebral thrombosis, cerebral embolism, cardiac arrest, stroke, transient ischemic attacks (TIA), hypertensive encephalopathy and so on.

4 Claims, No Drawings

USE OF MACROLIDES FOR THE TREATMENT OF CEREBRAL ISCHEMIA

This application is a 371 of PCT/JP93/01886 filed Dec. 24, 1993.

TECHNICAL FIELD

This invention relates to a new use of macrolide compounds.

In more detail, this invention relates to a new use of macrolide compounds for preventing or treating cerebral ischemic disease.

Accordingly, this invention provides a new use of the macrolide compounds for preventing or treating cerebral ischemic disease.

BACKGROUND ART

The macrolide compounds used in this invention are known and disclosed, for example, in European Patent Publication No. 0184162 and International Publication No. WO 89/05304.

These known macrolide compounds include the fermentation products, such as FR-900506, FR-900520, FR-900523 and FR-900525 which were isolated from microorganisms belonging to genus Streptomyces, such as Streptomyces tsukubaensis No. 9993 (FERM BP-927) or Streptomyces hygroscopicus subsp. yakushimaensis No. 7238 (FERM BP-928), and their related compounds prepared from these fermentation products.

These macrolide compounds were indicated inter alia for use in the treatment of rejection to transplantation, autoimmune diseases and infectious diseases caused, for example, by Aspergillus, Fusarium, Trichophyton, and the like.

DISCLOSURE INVENTION

The inventors of this invention have surprisingly found that the macrolide compounds mentioned hereinbelow have a neuroprotective activity, and that they are useful for preventing or treating cerebral ischemic disease, particularly cerebral infarction. The macrolide compounds used in this invention can be represented by the following general formula (I).

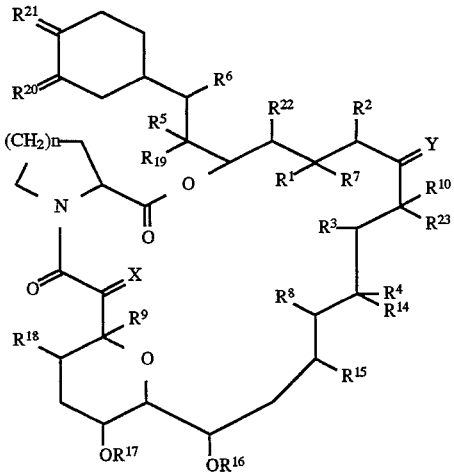

wherein each vicinal pair of substituents [$R^1$ and $R^2$], [$R^3$ and $R^4$], [$R^5$ and $R^6$] independently a) represent two vicinal hydrogen atoms, or b) form a second bond between the vicinal carbon atoms to which they are attached;

in addition to its significance above, $R^2$ may represent an alkyl group;

$R^7$ represents H, OH, protected hydroxy or O-alkyl, or in conjunction with $R^1$ it may represent =O;

$R^8$ and $R^9$ independently represent H or OH;

$R^{10}$ represents H, alkyl, alkyl substituted by one or more hydroxyl groups, alkenyl, alkenyl substituted by one or more hydroxyl groups, or alkyl substituted by =O;

X represents O (H, OH), (H, H) or —CH$_2$O—;

Y represents O (H, OH), (H, H), N—NR$^{11}$R$^{12}$ or N—OR$^{13}$;

$R^{11}$ and $R^{12}$ independently represent H, alkyl, aryl or tosyl;

$R^{13}$, $R^{14}$, $R^{15}$, $R^{16}$, $R^{17}$, $R^{18}$, $R^{19}$, $R^{22}$ and $R^{23}$ independently represent H or alkyl;

$R^{20}$ and $R^{21}$ independently represent O, or they may independently represent ($R^{20}$a, H) and ($R^{21}$a, H) respectively; $R^{20}$a and $R^{21}$a independently represent OH, O-alkyl or OCH$_2$OCH$_2$OCH$_2$OCH$_3$ or $R^{21}$a is protected hydroxy;

in addition, $R^{20}$a and $R^{21}$a may together represent an oxygen atom in an epoxide ring;

n is 1, 2 or 3;

in addition to their significances above, Y, $R^{10}$ and $R^{23}$, together with the carbon atoms to which they are attached, may represent a 5- or 6- membered N—, S— or O— containing heterocyclic ring, which may be saturated or unsaturated, and which may be substituted by one or more groups selected from alkyl, hydroxy, alkyl substituted by one or more hydroxyl groups, O-alkyl, benzyl and —CH$_2$Se(C$_6$H$_5$).

The specific examples of the definitions of compound (I) and the preferred working modes of the invention are described in detail below.

The term "lower" as used in this specification means, unless otherwise indicated, any number of carbon atoms between 1 and 6, inclusive.

Suitable "alkyl" means straight or branched saturated aliphatic hydrocarbon residue and may include lower alkyl such as methyl, ethyl, propyl, isopropyl, butyl, isobutyl, pentyl, neopentyl, hexyl, and the like.

Suitable "alkenyl" means straight or branched unsaturated aliphatic hydrocarbon residue having one double bond and may include lower alkenyl such as vinyl, propenyl (e.g. allyl), butenyl, methylpropenyl, pentenyl, hexenyl, and the like.

Suitable "aryl" may include phenyl, tolyl, xylyl, cumenyl, mesityl, naphthyl, and the like.

Suitable examples of the protective group in the "protected hydroxyl group" may include:

1-(lower alkylthio)(lower)alkyl groups such as lower alkylthiomethyl groups (e.g. methylthiomethyl, ethylthiomethyl, propylthiomethyl, isopropylthiomethyl, butylthiomethyl, isobutylthiomethyl, hexylthiomethyl, etc.), more desirably C$_1$–C$_4$ alkylthiomethyl groups, and most desirably methylthiomethyl; tri-substituted silyl groups such as tri(lower)alkylsilyl groups (e.g. trimethylsilyl, triethylsilyl, tributylsilyl, tert-butyl-dimethylsilyl, tri-tert-butylsilyl, etc.), lower alkyl-diarylsilyl groups (e.g. methyldiphenylsilyl, ethyldiphenylsilyl, propyldiphenylsilyl, tert-butyldiphenylsilyl, etc.), more desirably tri(C$_1$–C$_4$)alkylsilyl and C$_1$–C$_4$ alkyldiphenylsilyl groups and most desirably tert-butyldimethylsilyl and tert-butyldiphenylsilyl; and acyl groups such as aliphatic acyl groups, aromatic acyl groups and aliphatic acyl groups substituted by aromatic groups, which are derived from carboxylic acids, sulfonic acids or carbamic acids.

The aliphatic acyl group may includes lower alkanoyl groups which may optionally have one or more suitable substituents such as carboxy (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo(lower)alkoxy(lower)alkanoyl groups which may optionally have one or more appropriate substituents such as lower alkyl (e.g. cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.), camphorsulfonyl, lower alkylcarbamoyl groups having one or more suitable substituents such as carboxy or protected carboxy, for example carboxy (lower)alkylcarbamoyl groups (e.g. carboxymethylcarbamoyl, carboxyethylcarbamoyl, carboxypropylcarbamoyl, carboxybutylcarbamoyl, carboxypentylcarbamoyl, carboxyhexylcarbamoyl, etc.), protected carboxy(lower)alkylcarbamoyl groups such as tri(lower)alkylsilyl(lower)alkoxycarbonyl(lower) alkylcarbamoyl groups (e.g. trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.), and so on.

The aromatic acyl group may include aroyl groups which may optionally have one or more suitable substituents such as nitro (e.g. benzoyl, toluoyl, xyloyl, naphthoyl, nitrobenzoyl, dinitrobenzoyl, nitronaphthoyl, etc.), arenesulfonyl groups which may optionally have one or more suitable substituent(s) such as halogen (e.g. benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.), and so on.

The aromatic group-substituted aliphatic acyl group may include ar(lower)alkanoyl groups which may optionally have one or more suitable substituent(s) such as lower alkoxy and trihalo(lower)alkyl (e.g. phenylacetyl, phenylpropionyl, phenylbutyryl, 2-trifluoromethyl-2-methoxy-2-phenylacetyl, 2-ethoxy-2-trifluoromethyl-2-phenylacetyl, 2-trifluoromethyl-2-propoxy-2-phenylacetyl, etc.), and so on.

Among the above-mentioned acyl groups, the more desirable acyl groups are $C_1$-$C_4$ alkanoyl groups which may optionally be substituted by carboxy, cyclo($C_5$-$C_6$)alkyloxy ($C_1$-$C_4$)alkanoyl groups having two ($C_1$-$C_4$)alkyl groups in the cycloalkyl moiety, camphorsulfonyl, carboxy($C_1$-$C_4$) alkylcarbamoyl groups, tri($C_1$-$C_4$)alkylsilyl($C_1$-$C_4$) alkoxycarbonyl($C_1$-$C_4$)alkylcarbamoyl groups, benzoyl which may have one or two nitro groups, halogen-substituted benzenesulfonyl groups, phenyl($C_1$-$C_4$)alkanoyl groups having $C_1$-$C_4$alkoxy and trihalo($C_1$-$C_4$)alkyl groups. Of these groups, the most desirable are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Suitable "5- or 6-membered N—, S— or O-containing heterocyclic ring" may include pyrrolyl, tetrahydrofuryl, and the like.

Preferred embodiments of the Symbols $R^1$ to $R^{10}$, $R^{14}$ to $R^{23}$, X, Y and n are as follows.

$R^1$ and $R^2$ are each hydrogen or combined to form a second bond;

$R^3$ and $R^4$ are combined to form a second bond;

$R^5$ and $R^6$ are combined to form a second bond;

$R^7$ is hydrogen, hydroxy, O-lower alkyl such as methoxy or protected hydroxy;

$R^8$ is hydrogen or hydroxy;

$R^9$ is hydroxy;

$R^{10}$ is methyl, ethyl, propyl, allyl or 2-oxopropyl;

$R^{14}$, $R^{15}$, $R^{16}$, $R^{17}$, $R^{18}$, $R^{19}$ and $R^{22}$ are each methyl;

$R^{20}$ is oxo or ($R^{20}$a, H), wherein $R^{20}$a is hydroxy or methoxy;

$R^{21}$ is ($R^{21}$a, H), wherein $R^{21}$a is hydroxy or protected hydroxy;

$R^{23}$ is hydrogen;

X is oxo, (H, OH) or (H, H);

Y is oxo; and n is 1 or 2.

The pharmaceutically acceptable salt of the compound (I) is a nontoxic salt, which may be the corresponding salt with an inorganic or organic base such as alkali metal salts (e.g. sodium salt, potassium salt, etc.), alkaline earth metal salts (e.g. calcium salt, magnesium salt, etc.), ammonium salt and amine salts (e.g. triethylamine salt, N-benzyl-N-methylamine salt, etc.), and so on.

Regarding the macrolide compounds (I), there may exist one or more conformers, or one or more stereoisomeric pairs such as optical and geometrical isomers due to the asymmetric carbon(s) or the double bond(s). Such conformers and isomers also fall within the scope of the invention.

Particularly, the most interesting compound is FR-900506 of the following formula.

(hereinafter, described as FK506)

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

Other preferable compounds are listed hereinbelow.

1,14-dihydroxy-12-[2-(4-hydroxy-3-methoxycyclohexyl)-1-methylvinyl]-23,25-dimethoxy-13,19,17,21,27-pentamethyl-11,28-dioxa-4-azatricyclo[22.3.1.0$^{4,9}$] octacos-18-ene-2,3,10,16-tetraone, 12-[2-(4-acetoxy-3-methoxycyclohexyl)-1-methylvinyl]-17-allyl-1,14-dihydroxy-23,25-dimethoxy-13,19,21, 27-tetramethyl-11,28-dioxa-4-azatricyclo[22.3.1.0$^{4,9}$]
octacos-18-ene-2,3,10,16-tetraone, 17-allyl-1,14-dihydroxy-23,25-dimethoxy-13,19,21,27-tetramethyl-12-[2-[4-(3,5-dinitrobenzoyloxy)-3-methoxycyclo-hexyl]- 1-methylvinyl]-11,28-dioxa-4-azatricyclo[22.3.1.0$^{4,9}$]octacos-18-ene-2,3,10,16-tetraone, 17-allyl-12-[2-[4-[(−)-2-trifluoromethyl-2-methoxy-2-phenylacetoxy]-3-methoxycyclohexyl]-1-methylvinyl]-1,14-dihydroxy-23,25-dimethoxy-13,19,21,27-tetramethyl-11,28-dioxa-4-azatricyclo[22.3.1.0$^{4,9}$]octacos-18-ene-2,3,10,16-tetraone, 17-ethyl-1,14-dihydroxy-12-[2-(4-hydroxy-3-methoxycyclo-hexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, and 17-ethyl-1,14,20-trihydroxy-12-[2-(3,4-dihydroxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

The macrolide compounds (I) of the present invention can be administered in a pure or impure form and in a single compound or a mixture thereof, preferably, in a pharmaceutical vehicle or carrier.

The pharmaceutical composition of this invention can be used in the form of a pharmaceutical preparation, for example, in solid, semisolid or liquid form, which contains the macrolide compounds of the present invention, as an active ingredient, in admixture with an organic or inorganic carrier or excipient suitable for external (topical), enteral, oral, intravenous, intramuscular, or parenteral applications. The active ingredient may be compounded, for example, with the usual non-toxic, pharmaceutically acceptable carriers for ointment, cream, plaster, tablets, pellets, capsules, suppositories, solutions (saline, for example), emulsion, suspensions (olive oil, for example), and any other form suitable for use. The carriers which can be used are water, wax, glucose, lactose, gum acacia, gelatin, mannitol, starch paste, magnesium trisilicate, talc, corn starch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in the pharmaceutical composition in an effective amount sufficient to produce the desired effect upon the process or condition of the diseases.

Mammals which may be treated by the present invention include livestock mammals such as cows, horses, etc., domestic animals such as dogs, cats, rats, etc. and humans, preferably humans.

For applying this composition to a human, it is preferable to apply it by oral, parenteral, enteral, intravenous, or intramuscular administration.

While the dosage of therapeutically effective amount of the macrolide compounds varies from and also depends upon the age and condition of each individual patient to be treated, in case of the systemic administration, a daily dose of about 0.0001–1000 mg, preferably 0.001–500 mg and more preferably 0.01–100 mg of the active ingredient is generally given for treating the diseases, and an average single dose of about 0.001–0.01 mg, 0.2–0.5 mg, 1 mg, 5 mg, 10 mg, 50 mg, 100 mg, 250 mg and 500 mg is generally administered. Daily doses for chronic administration in humans will be in the range of about 0.05–50 mg/kg/day, preferably 0.1–10 mg/kg/day, and more preferably 0.1–0.3 mg/kg/day.

And further, it is considered that the compounds disclosed in the following patent applications such as EP-A-353678, Japanese Patent Application No. 2(1990)-74330, PCT/GB90/01262, EP-A-4135532, PCT/JP91/00314, British Patent Applications No. 9012963.6, No. 9014136.7, No. 9014681.2, No. 9014880.0, No. 9014881.8, No. 9015098.8, No. 9016115.9, and No. 9016693.5, EP-A-323865, EP-A-349061, EP-A-358508, EP-A-364031, EP-A-364032, EP-A-378317, EP-A-378320, EP-A-378321, EP-A-388153, EP-A-396399, EP-A-396400, EP-A-399579, EP-A-403242, EP-A-428365, EP-A-356399, GB 2225576 A, EP-A-402931, EP-A-427680, EP-A-445975, EP-A-455427, EP-A-463690, EP-A-464895, EP-A-466365, EP-A-478235, OEP-A-480623, EP-A-509753, EP-A-515071, EP-A-520554, EP-A-526934, EP-A-530888, EP-A-532089, and EP-A-532088, WO92/06992, WO92/20688, WO93/04679, WO093/05059, and WO093/04680, U.S. Pat. No. 5149701, German Patent Applications A-4021404, A-4028664, A-4028665, A-4028666, A-4028667, A-4028675, A-4028676, A-4028677, A-4028678, and A-4039587; and so on, are also useful for the diseases shown in the present specification.

In order to exhibit the usefulness of the present invention, the activity of the representative compound of the macrolide compounds (I) against neuropathological damage on coronal sections of brain is shown below.

METHODS (1) Studies were performed on male Sprague-Dawley rats (300–350 g; Charles River). Animals were anaesthetised with pentobarbitone (Sagittal; 60 mg/kg; i.p.) prior to the administration of FK506 (10 mg/kg) or vehicle (50% ethanol in physiological saline containing Tween-80; final volume of 1 ml/kg) by the intraperitoneal route. Thirty minutes later, endothelin-1 (60 pmol in 3 µl) was injected over 1 minute via a 31-gauge cannula stereotaxically placed into the piriform cortex approximately 0.5 am dorsal to the middle cerebral artery (0.2 mm anterior and 5.2 am lateral to bregma; and 7.5 am below the dura). The cannula was left in situ for a further 5 minutes before being slowly withdrawn over 2–3 minutes, and the scalp was then sutured. Rats were maintained at 37°–38° C. throughout the procedure by means of a heating blanket attached to thermometer placed in the animal's rectum. Upon completion of surgery, the animals were placed in an incubation chamber maintained at 37° C. until they had fully recovered from the anaesthetic before being returned to their home cage.

Three days after injection, the rats were deeply anaesthetised with methohexitone (Brietal; 75 mg/kg; i.p.) prior to transcardiac fixation with 4% formaldehyde in phosphate buffered saline. The brains were removed intact, then cryostat sectioned (20 µm) in the coronal plane. Brain sections were subsequently stained by cresyl violet. Sections were examined by light microscopy, and neuropathological damage was estimated by assessment of infarct volume by an observer who was unaware of the treatment group under examination.

Effect of FK506 (10 mg/kg) upon the volume of ischemic damage produced by the perivascular microapplication of endothelin-1 onto the rat middle cerebral artery:

|  | Total Hemisphere | Striatum | Neocortex |
| --- | --- | --- | --- |
| Vehicle (n = 7) | 116 ± 12 | 25 ± 3 | 91 ± 10 |
| FK506 (n = 8) | 62 ± 12** | 24 ± 2 | 38 ± 11** |

Data presented are mean infarct volume (mm$^3$) ± s.e.m. for n animals per treatment group.
**; p ≤ 0.01 Student's t-test with Bonferronni statistic for multiple comparisons.

FK506 reduced the cortical infarct volume by 58% whereas no effect on striatal infarct volume was observed. The total hemispheric volume of ischemic damage was reduced by 47% in the FK506 treated group.

(2) Animals (280–300 g, male, Sprague-Dawley; Charles River, U.K.) were anaesthetized with a gaseous mixture of halothane in nitrous oxide and oxygen (1–2% in 80:20 v/v) in order to insert cannulae into the right femoral vein. With anaesthesia continuing, the rats were placed in a stereotaxic frame, a craniectomy performed and endothelin-1 (120 pmol in 3 μl) was injected over 3 minutes via a 29-guage cannula stereotaxically placed into the piriform cortex approximately 0.5 mm dorsal to the middle cerebral artery (0.2 mm anterior and 5.2 mm lateral to bregma; and 7.5 mm below the dura). Rats received an intravenous injection of FK506 (0.1, 0.3, 1.0 mg/kg) or intravenous vehicle (10% polyoxyethylenehydrogenated castor oil 60 (400 mg/ml)/ ethanol in physiological saline; 1 ml/kg) one minute after the completion of the endothelin injection. The cannula was left in situ for a further 5 minutes before being slowly withdrawn, and the scalp sutured closed. Rats were maintained at 37°–38° C. throughout the procedure using a thermostatically-controlled heating blanket attached to a rectal thermometer. Upon completion of surgery, animals were placed in an incubator in which body temperature was maintained at 37° C. until they had fully recovered from the anaesthetic. Three days after injection, the rats were deeply anaesthetized with pentobarbitone prior to transcardiac fixation with paraformaldehyde (4% in phosphate buffered saline). The brain was then removed intact and immersed in fixative containing 10% sucrose for at least 24 hrs prior to cryostat sectioning at 20 μm and histological staining with cresyl violet. Sections were examined under light microscopy by an individual who was unaware of the treatment group. The extent of the infarction, at 8 predetermined levels was annotated onto enlarged diagrams and the volume of infarction calculated by integrating the cross-sectional area of damage at each stereotaxic level and the distances between the various levels. The volume of ischemic brain damage In the cortex was reduced by 62% (0.1 mg/kg), 58% (0.3 mg/kg) and 65% (1.0 mg/kg) when compared with vehicle controls.

The following examples are given for the purpose of illustrating the present invention.

EXAMPLE 1

| FK506 | 1 g |
|---|---|
| Hydroxypropyl methylcellulose 2910 (TC-5R) | 1 g |
| Lactose | 2 g |
| Croscarmellose sodium (Ac-Di-Sol) | 1 g |

FK506 (1 g) was dissolved in ethanol (10 ml), and thereto was added hydroxypropyl methylcellulose 2910 (TC-5R) (1 g) to prepare a suspension. To this suspension was added dichloromethane (5 ml) to prepare a homogeneous solution. Lactose (2 g) and croscarmellose sodium (Trade Mark: Ac-Di-Sol, maker: Asahi Chemical Industry) were homogeneously suspended to this solution, and then the organic solvent was removed by evaporation. The residual product was dried under reduced pressure for 10 hours by vacuum dryer, milled for 2 minutes by coffee mill and then passed through a sieve (32 mesh) to give the solid dispersion composition of FK506 (5 g) (hereinafter, described as SDF). This composition was capsulated by a conventional manner to provide capsules containing 1 mg or 5 mg of FK506 per each capsule.

EXAMPLE 2

| FK506 | | 10 mg |
|---|---|---|
| HCO-60 (polyoxyethylenehydrogenated castor oil 60) | | 400 mg |
| Ethanol | to | 1 ml |

The solution comprising the ingredients stated above is prepared by dissolving the FK506 and HCO-60 in ethanol by a conventional manner. It can be administered via i.v. infusion by diluting with a proper volume of physiological saline.

EXAMPLE 3

| FK506 | | 2 mg |
|---|---|---|
| Polysorbate | | 50 mg |
| Propylene glycol | to | 1 ml |

The above solution Is prepared in a similar manner of the Example 2.

The present invention provides useful drugs for preventing or treating cerebral ischemic disease, in other word, brain damage caused by ischemia, such as cerebral infarction. So, they are useful when the following diseases or injury occur. That is, head injury, hemorrhage in brain such as subarachnoid hemorrhage or intracerebral hemorrhage, cerebral thrombosis, cerebral embolism, cardiac arrest, stroke, transient ischemic attacks (TIA), hypertensive encephalopathy and so on.

We claim:

1. A method for preventing or treating cerebral ischemic disease, comprising administering to a patient in need thereof, a macrolide compound of the formula:

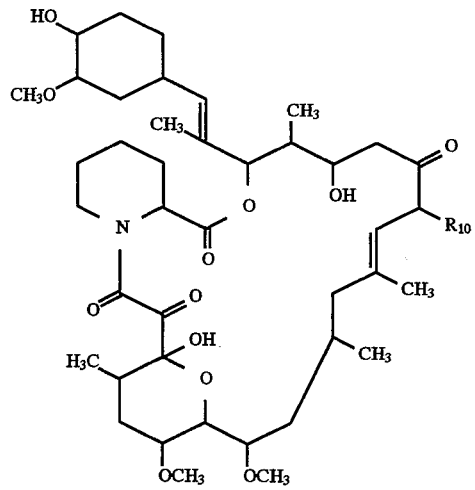

wherein $R^{10}$ is methyl, ethyl, propyl or allyl, or a pharmaceutically acceptable salt thereof.

2. The method of claim 1, wherein said macrolide compound is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$] octacos-18-ene-2,3,10,16-tetraone.

3. The method of claim 1, wherein said cerebral ischemic disease is cerebral infarction.

4. The method of claim 1, wherein said method is for treating cerebral ischemic disease.

* * * * *